United States Patent [19]
Igarashi et al.

[11] Patent Number: 5,453,512
[45] Date of Patent: Sep. 26, 1995

[54] METHOD OF PRODUCING 2-AMINO-3-NITRO-5-HALOGENOPYRIDINE

[75] Inventors: Yoshio Igarashi, Chiba; Makoto Shimoyamada, Fukushima; Motoki Takashima, Fukushima; Tetsuya Suzuki, Fukushima, all of Japan

[73] Assignee: Ichikawa Gosei Chemical Co., Ltd., Chiba, Japan

[21] Appl. No.: 168,205

[22] Filed: Dec. 17, 1993

Related U.S. Application Data

[60] Division of Ser. No. 924,556, Aug. 5, 1992, Pat. No.5,290,943, which is a continuation-in-part of Ser. No. 836,968, Feb. 19, 1992, abandoned.

[30] Foreign Application Priority Data

Feb. 21, 1991 [JP] Japan ................ 3-027563
Aug. 6, 1991 [JP] Japan ................ 3-196696
Jul. 23, 1992 [JP] Japan ................ 4-196829

[51] Int. Cl.$^6$ ................ C07D 213/75
[52] U.S. Cl. ................ 546/309
[58] Field of Search ................ 546/309

[56] References Cited

U.S. PATENT DOCUMENTS 4,086,078  9/1978  Bollinger et al. ................ 504/130

FOREIGN PATENT DOCUMENTS 0343894  11/1989  European Pat. Off. ................ 546/309
1400540   7/1975  United Kingdom ................ 546/309

OTHER PUBLICATIONS

Chemical Abstracts, vol. 64, Abstract No, 19,571b, Jun. 1966.
J. Am. Chem. Soc., vol. 79 (1957), pp. 6422–6424.
B. A. Fox et al., Organic Synthesis, Col. 1, vol. 5, p. 346, 1976.
L. H. Fieser, "Reagents for Organic Synthesis", vol. 1 (1967), pp. 967–970.
Placek et al., Chem. Ber., vol. 61 (1928), pp. 1815–1816.
Okamoto et al., Chem. Pharm. Bul., vol. 14 (1966) p. 527.
Journal of Medical Chemistry, vol. 26, 1983, pp. 538–544, cpd 5, sheme I (to form 71–821)).
Chemical Abstracts, vol. 102, No. 9, 4 Mar. 1985, Columbus, Ohio U.S. Abstract No. 11049e, (abstract); & Journal of the American Chemical Society., vol. 79, 1957, pp. 6421–6429-H. Graboyes et al.
Journal of Medicinal Chemistry, vol. 14, No. 10, October 1971, pp. 963–968, R. B. Moffett et al.
Journal of Pharmaceutical Sciences, vol. 60, No. 11, Nov. 1971, pp. 1723–1725, W. S. Dorsey et al.
Chemicke Zvesti, vol. 31, No. 2, 1977, pp. 254–264, P. Tomasik et al.
Indian Journal of Chemistry, vol. 22B, No. 2, Feb. 1983, pp. 117–120, P. Jayaprasad et al.
Journal of Heterocyclic Chemistry, vol. 24, 1987, pp. 215–217, J. P. Sanchez et al.
Pharmazie, vol. 45, 1990, Berlin. DD, pp. 441–442, G. Daidone et al.
Journal of the American Chemical Society, vol. 66, 1944, Washington, D.C. US pp. 1479–1484, W. T. Caldwell et al.
Journal of Organic Chemistry, vol. 41, No. 1, 1976, pp. 93–96 T. J. Kress et al.
Journal of the American Chemical Society, vol. 71, 1949, pp. 1885–1888, J. R. Vaughan et al.
Case, JACS, vol. 68 (1946), p. 2576.

Primary Examiner—C. Warren Ivy
Assistant Examiner—Zinna N. Davis
Attorney, Agent, or Firm—Sixbey, Friedman, Leedom & Ferguson; Gerald J. Ferguson, Jr.; Joan K. Lawrence

[57] ABSTRACT

A 2-amino-3-nitro-5-halogenopyridine is formed from a 2-acylaminopyridine by way of a 2-acylamino-5-halogenopyridine. The 2-acetamido-5-bromopyridine may be formed from the 2-acylaminopyridine by way of a 2-acylaminopyridinium-HBr$_3$ salt.

4 Claims, No Drawings

METHOD OF PRODUCING 2-AMINO-3-NITRO-5-HALOGENOPYRIDINE

This is a divisional application of Ser. No. 07/924,556, filed Aug. 5, 1992, now U.S. Pat. No. 5,290,943 which itself is a continuation-in-part application of application Ser. No. 836,968 filed Feb. 19, 1992 now abandoned.

BACKGROUND OF THE INVENTION

1. Field of the Invention

The present invention relates to industrially useful 2-aminopyridine derivatives and methods of producing the same.

2. Description of the Prior Art 2-aminopyridine derivatives are useful as starting materials for medicines, agricultural chemicals, and physiologically active materials. In particular, when the nitro group is reduced, 2-amino-3-nitropyridines form 2,3-diaminopyridines which can produce imidazopyridines and pyridotriazols when processed with carboxylic acid and nitrous acid, respectively. These compounds are known to have physiolosical activities.

However, when 2-aminopyridines are nitrated to form 2-amino-3-nitropyridines, the yield of the aimed 3-nitro compounds is low, while a large amount of 5-nitro compounds are formed. Accordingly, it is preferable to use a method comprising the steps of blocking the 5-position of 2-aminopyridines with a halogen atom such as bromine or chlorine, nitrating them to produce 2-amino-3-nitro-5-halogenopyridines (V), and then removing the halogen atom before or after the ring-closure reaction. This method is used in Graboyes et al., J. Am. Chem. Soc., 79, 6421 (1957) and J. B. Ziegler et al., J. Am. Chem. Soc., 71, 1891 (1949).

Nevertheless, even when 2-aminopyridines are halogenated to form 2-amino-5-halogenopyridines (VI), the known methods have many problems.

Namely, B. A. Fox et al (Org. Synth., Col. Vol.5, 346) report the synthesis of 2-amino-5-bromopyridine (VId) by bromination of 2-aminopyridine. However, due to the formation of 2-amino-3,5-dibromopyridine as a by-product, the yield is as low as 62%. Accordingly, such a purifying operation as petroleum ether cleaning is necessary. Also, the above-mentioned Graboyes et al use the method of Case [J. Am. Chem. Soc., 68, 2574 (1946)] and brominate 2-amino-4-methylpyridine in ethanol. Since dibromides are formed in this method, a crude product is washed with ligroin before it is subjected to recrystallization in cyclohexane. This method is industrially unfavorable in that the purificatin process is troublesome. While A. D. Dunn et al [J. Prakt. Chem., 331, 369 (1989)] react 2-amino-4-methylpyridine with hydrogen peroxide in concentrated hydrobromic acid to produce 2-amino-4-methyl-5-bromopyridine (VIa), the yield thereof is as low as 40% while as high as 23% of dibromides are formed as by-products. Also, when 2-amino-6-methylpyridine is brominated, isomers and dibromides are formed as by-products.

On the other hand, there have been many problems in the conventional methods for chlorinating 2-aminopyridines. For example, in T. Batkowski, Rocz. Chem., 42, 2079 (1968), while 2-aminopyridine is reacted with chlorine in ethanol to form 2-amino-5-chloropyridine, the yield is only 64% and not sufficient. Also, in J. P. English et al., J. Am. Chem. Soc., 68, 453 (1946), while 2-aminopyridine is reacted with chlorine in 20% sulfuric acid, the yield is as low as 54% and the operation is troublesome since by-product, 2-amino-3,5-dichloropyridine, is removed by washing with carbon tetrachloride. Further, in German Patent Publication DE 2,141,634 (1972) to C. Cottel et al, while various 2-aminopicolines are processed with hydrogen peroxide in concentrated hydrochloride so that corresponding 5-chlorinates are synthesized, recrystallization with n-hexane is necessary and the yield is low. In T. J. Kress et al., [J. Org. Chem., 41, 93 (1976) and German Patent Publication DE 2,520,726 (1975)], 2-aminopicolines are chlorinated in 72% sulfuric acid to form corresponding 5-chlorinates with relatively good yields. However, this method is disadvantageous in that a low reaction temperature (−33° C.) is necessary.

As described in the foregoing, a satisfactory method for producing 2-amino-5-halogenopyridines (VI) has not been known. Also, since their production is difficult, 2-amino-3-nitro-5-halogenopyridines (V), which are their nitro-derivatives, have not easily been produced at a low cost on an industrial scale.

SUMMARY OF THE INVENTION

The object of the present invention is to provide an efficient method of producing 2-amino-3-nitro-5-halogenopyridines (V).

The present invention provides a method of producing a 2-amino-3-nitro-5-halogenopyridine expressed by general formula (V)

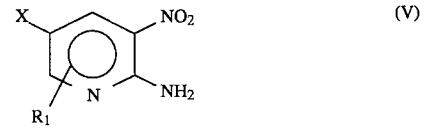

wherein $R_1$ is hydrogen or at least one lower alkyl group connected to 4-position and/or 6-position, $R_2$ is an alkyl group or an unsubstituted or substituted phenyl group, and X is a halogen, said method comprising the steps of providing, as a starting material, a 2-acylaminopyridine expressed by general formula (I)

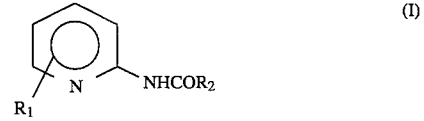

wherein $R_1$ and $R_2$ are defined in the same manner as in the general formula (V) and forming, as an intermediate, a 2-acylamino-5-halogenopyridine expressed by general formula (II)

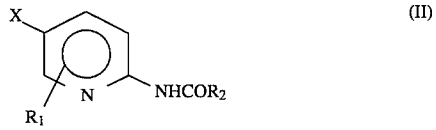

wherein $R_1$ and $R_2$ are defined in the same manner as in the general formula (I) and X is a halogen.

Due to the contribution of their amino group, 2-aminopyridines are very active and easily attacked by electrophilic reagents such as halogens. Accordingly, substitution is likely to occur in their 3-position and -position which are active sites. Therefore, it is difficult to selectively introduce a substituent to their 5-position. The amino group may be acylated in order to reduce the contribution thereof. Conventionally, it has been known, mainly in the bromination of anilines and the like, that preferable results are obtained when the amino group is acetylated before being brominated. For example, J. R. Johnson et al [Org. Synth., 1, 111 (1941)] acetylate the amino group of p-toluidine, brominate the acetylated product, and then synthesize 2-bromo-4-methylaniline by hydrolysis.

The inventors of the present invention have studied whether or not the above method is applicable to 2-aminopyridines expressed by general formula (I') wherein $R_1$ is defined in the same manner as in the above-mentioned formula (I). 2-aminopyridines have been acylated by acid anhydrides like acetic anhydride or acid halides to produce 2-acylaminopyridines quantitatively. For example, the acetylation by acetic anhydride is indicated by Seide et al [Chem. Bet., 57, 792 (1924)] and G. Lang [German Patent Publication DE 2331009 (1974)].

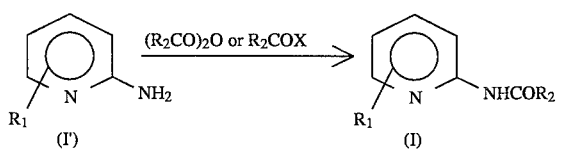

Firstly the inventors have found that, when a 2-acylaminopyridine reacts with bromine, a 2-acylamino-5-bromopyridine (II) expressed by general formula (II) and a 2-acylaminopyridinium-$HBr_3$ salt (III) expressed by general formula (III) wherein $R_1$ and $R_2$ are defined in the same manner as in the above-mentioned formula (I) are obtained.

The salt (III) is novel. It has not conventionally been known to synthesize the 2-acylamino-5-bromopyridine (II) and 2-acylaminopyridinium-$HBr_3$ salt (III) based on the reaction of the 2-acylaminopyridine (I) with molecular bromine.

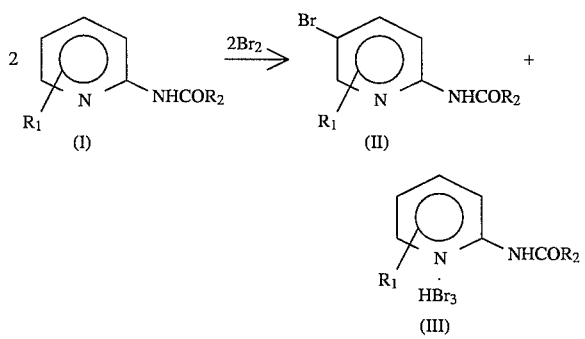

It has conventionally been known to process a pyridine with hydrogen bromide and then add bromine thereto to form a pyridinium-$HBr_3$ salt [L. H. Fieser, "Reagents for Organic Synthesis," vol. 1, 967 (1967)]. However, it has not been known that the 2-acylaminopyridine (I) forms a similar salt. The 2-acylaminopyridinium-$HBr_3$ salt (III) can be produced by a method comprising the steps of reacting gaseous hydrogen bromide or concentrated hydrobromic acid with the 2-acylaminopyridine (I) to form a 2-acylaminopyridinium-HBr salt (IV) and then isolating it or continuously adding bromine thereto.

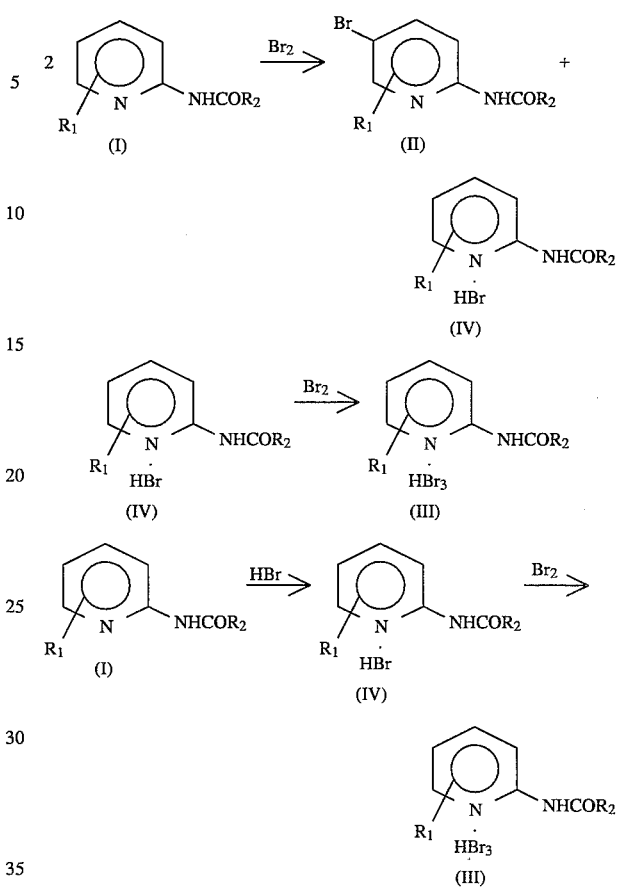

The inventors have studied the 2-acylaminopyridinium-$HBr_3$ salt (III) and found that this compound gradually decomposes in a protic polar solvent such as water or an alcohol to form the 2-acylamino-5-bromopyridine (II).

When the 2-acylaminopyridine (I) reacts with bromine in a chain hydrocarbon such as n-hexane, n-octane, or n-heptane, a hydrocarbon halide such as dichloromethane, dichloroethane, trichloroethane, chloroform, or carbon tetrachloride, or an aromatic compound such as benzene, chlorobenzene, o-dichlorobenzene, or nitrobenzene, a mixture of the 2-acylamino-5-bromopyridine (II) and 2-acylaminopyridinium-$HBr_3$ salt (III) is formed. They can be subjected to solid-liquid separation according to the kind and amount of the solvent used and the temperature. This is due to the fact that 2-acylamino-5-bromopyridine (II) exhibits a great solubility with respect to these solvents while the 2-acylaminopyridinium-$HBr_3$ salt (III) has a low solubility. Also, when the 2-acylaminopyridine (I) is dissolved or suspended in such a solvent and then hydrogen bromide gas is blown thereinto or concentrated hydrobromic acid and bromine are successively added dropwise thereto, the 2-acylaminopyridinium-$HBr_3$ salt (III) is formed.

When stirred in a protic polar solvent like water or an alcohol, the 2-acylaminopyridinium-$HBr_3$ salt (III) or a mixture of the 2-acylamino-5-bromopyridine (II) and 2-acylaminopyridinium-$HBr_3$ (III) salt obtained by the reaction of the 2-acylaminopyridine with bromine is gradually converted into the 2-acylamino-5-bromopyridine (II). The reaction temperature is preferably within the range between room temperature and 60° C. The reaction proceeds slowly when the temperature is low, while a side reaction like the hydolysis of amides proceeds when it is high. After the completion of the reaction, when the aimed object is in the form of slurry, it is subjected to solid-liquid separation and then washed with water. When the aimed object is oily, it is separated as it is or extracted by a solvent and then purified. When neutralization is effected after the completion of the reaction, the unreacted 2-acylamino-5-bromopyridinium-HBr$_3$ salt (III) becomes the 2-acylaminopyridine (I) which can be collected when necessary.

The reaction between the 2-acylaminopyridine (I) or bromine can also be effected in a protic polar solvent like water or an alcohol. In this case, the 2-acylaminopyridinium-HBr$_3$ salt (III) is converted into the 2-acylamino-5-bromopyridine (II) at the same time. However, when generated in water, the 2-acylaminopyridinium-HBr$_3$ salt (III) becomes a hard crystal having a large particle size and a low dispersibility. Accordingly, the reaction thereof tends to proceed slowly. In the case of bromination in the water-nonpolar solvent mixture system, the 2-acylamino-5-bromopyridine (II) generated therefrom can be collected by such an operation as washing or concentrating since it can dissolve in the nonpolar solvent.

As a result of further studies, the inventors have found that, when the reaction of the 2-acylaminopyridine (I) with bromine is effected in an alkaline buffer solution, a nucleus bromination proceeds initiatively to form the desired 2-acylamino-5-bromopyridine (II) without generating the 2-acylaminopyridinium-HBr$_3$ salt (III).

As the alkaline buffer, Na$_2$HPO$_4$ (disodium hydrogen phosphate), CH$_3$CO$_2$Na (sodium acetate), or the like can be used. In either case, the 2-acylamino-5-bromopyridine (II) can be obtained with a good yield. Also, since the pH-fluctuation is small due to the buffer effect, a strong alkali like sodium hydroxide can be added to the alkaline buffer for the synthesis of the aimed product. The reaction can be effected in a water solvent, in a two-layer system of water-nonpolar solvent, or in a protic polar solvent like acetic acid or alcohol. When the method of the present invention is used in a water solvent, various 2-acylamino-5-bromopyridines (II) can be produced with a good yield and a remarkably excellent selectivity without forming 2-acylamino-3,5-dibromopyridines which are dibromides.

Conventionally, as the synthesis of 2-acylamino-5-bromopyridines, that of 2-acetamido-4,6-dimethyl-5-bromopyridine (IIc) by a method based on the exposure of 2-acetamido-4,6-dimethylpyridine (Ic) to light and the reaction of N-bromosuccinimide in the presence of benzoyl peroxide has been reported by R. P. Mariella et al [J. Am. Chem. Soc., 74, 1916 (1952)]. Also, the synthesis of 2-acetamido-5-bromopyridine (IId) by a method based on the use of 2-acetamidopyridine (Id) and bromine water has been reported by Placek et al [Chem. Ber., 61, 1815 (1928)]. However, none of these methods is industrially satisfactory.

The inventors have effected the halogenation of 2-acylaminopyridines by using chlorine in the presence of the above-mentioned alkaline buffer and obtained the aimed 2-acylamino-5-chloropyridines (II) with a good yield and a high selectivity. Conventionally, as the synthesis of 2-acylamino-5-chloropyridines, only that of 2-acetamido-4,6-dimethylpyridine by the use of N-chlorosuccinimide has been reported by W. A. Bolhofer et al [J. Med. Chem., 26, 538 (1983)]. Thus, the method of the present invention is novel.

The method of the present invention can also produce a new 2-acylamino-5-halogenopyridine expressed by general formula (II)

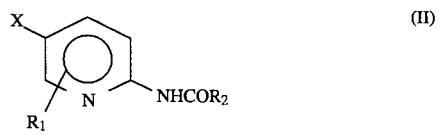

wherein R$_1$ is halogen or at least one lower alkyl group connected to 4-position and/or 6-position, R$_2$ is an alkyl group or an unsubstituted or substituted phenyl group, and X is a halogen, R$_1$ being a lower alkyl group connected to 4-position or 6-position when X is bromine and R$_1$ being a lower alkyl group connected to 4-position or 6-position when X is chlorine.

The halogenation of 2-acylaminopyridines (II) in the presence of the alkaline buffer in accordance with the present invention can be effected in various solvent systems. For example, a protic polar solvent like water, alcohol, or acetic acid; a non-protic polar solvent like dimethylformamide; and a nonuniform solvent system of water-nonpolar solvent can be used. The reaction temperature is preferably in the range of 0°–60° C. and more preferably in the range of 0°–20° C. When chlorination is effected in a single solvent system like water or alcohol, it is preferable that, after the reaction, the pH is adjusted to an acidic value or the system is heated.

As explained in the foregoing, the method of producing the 2-acylamino-5-halogenopyridine (II) in accordance with the present invention is industrially superior to the conventional methods of producing the same.

As a result of further studies, the inventors have found that, when the 2-acylamino-5-halogenopyridine (II) obtained by these methods is hydrolyzed under an acidic or alkaline condition, a 2-amino-5-halogenopyridine (VI) expressed by general formula (VI), wherein R$_1$ and X are defined in the same manner as in the above-mentioned general formula (II), is obtained with a good yield.

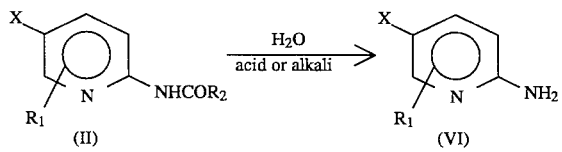

In the above-mentioned paper, Mariella et al have reported the synthesis of 2-acetamido-4,6-dimethyl-5-bromopyridine (VIc) by an alkaline hydrolysis of 2-amino-4,6-dimethyl-5-bromopyridine (IIc). Also, W. T. Caldwell et al [J. Am. Chem. Soc., 66, 1479 (1974)] have reported an acidic hydrolysis of 2-acetamido-5-bromopyridine (IId). However, the synthesis of the 2-amino-5-halogenopyridine (VI) expressed by general formula (VI) by the hydrolysis of 2-acylamino-5-halogenopyridine (II) expressed by general formula (II) has not been known heretofore.

Hydrochloric acid, sulfuric acid, hydrobromic acid, or the like can be used as an acid for the hydrolysis. In view of side reactions and economy, hydrochloric acid is preferable. In this case, since the reaction mixture has become a hydrochloride or the like of the 2-amino-5-halogenopyridine (VI), it is neutralized by an alkali and deposited as a crystal which is then subjected to solid-liquid separation. Sodium hydroxide, potassium hydroxide, sodium carbonate, potassium carbonate, or the like can be used as an alkali for the hydrolysis. In this case, since the reaction mixture has become a free alkali, it is subjected to solid-liquid separation as it is or concentrated after solvent-extraction.

This method is a novel synthesis route for the 2-amino-5-halogenopyridine (VI) expressed by general formula (VI).

The inventors have found that, when the 2-acylamino-5-halogenopyridine (II) is processed in sulfuric acid-nitric acid, it is hydrolyzed and nitrated at the same time to form a 2-amino-3-nitro-5-halogenopyridine (V) expressed by general formula (V) wherein $R_1$ and X are defined in the same manner as in the above-mentioned general formula (II).

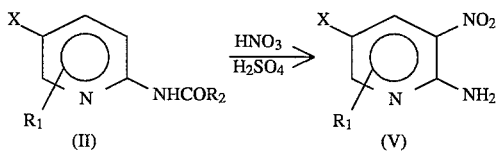

The above-cited Fox et al and Graboyes et al have obtained the 2-amino-3-nitro-5-bromopyridine (V) by the mixed acid nitration of the 2-amino-5-bromopyridine (VI). The nitration reaction of the 2-acylamino-5-halogenopyridine (II) has not been known heretofore. For the first time, the inventors have found the fact that the aimed 2-amino-3-nitro-5-halogenopyridine (V) can be obtained by a single step. The nitration reaction is preferably effected at a temperature within the range between room temperature and 60° C. The rate of reaction becomes low when the temperature is lower than this range, while the nitric acid gas generated in the system evaporates away and the yield is decreased when the temperature is higher than this range. More preferably, the reaction temperature is within the range between room temperature and 40° C. To the 2-acylamino-5-halogenopyridine (II), concentrated nitric acid can be used within the range of 0.5–1.2 equivalent mole and preferably within the range of 0.8–1.0 equivalent mole. This is because the yield of the aimed 2-amino-3-nitro-5-halogenopyridine (V) is decreased when a lower amount of nitric acid is used, while a greater amount of by-products is produced when a greater amount of nitric acid is used. To the 2-acylamino-5-halogenopyridine (II), concentrated sulfuric acid can be used within the range of 10–20 equivalent moles. The reaction does not proceed sufficiently when the sulfuric acid is used in an amount lower than that range, while the amount greater than that range is uneconomical.

The reaction can be traced by a method comprising the steps of sampling the reaction liquid, neutralizing the sample, subjecting the neutralized sample to solvent-extraction, and then analyzing the extracted layer by gas chromatography. After the completion of the reaction, the contents are dispersed in cooled water or iced water and the crystal, which is deposited after neutralization with an aqueous solution of an alkali such as sodium hydroxide, sodium carbonate, sodium hydrogencarbonate, or ammonia, is subjected to solid-liquid separation.

When this method is used, it is unnecessary to employ a two-step process comprising the steps of hydrolyzing the 2-acylamino-5-halogenopyridine (II), i.e. a precursor, to form the 2-amino-5-halogenopyridine (VI) and then nitrating the latter by a known method. Therefore, the 2-amino-3-nitro-5-halogenopyridine (V) can be produced easily at a low cost in accordance with the method of the present invention.

The 2-acylamino-5-halogenopyridine (II) produced by the method of the present invention can be subjected to nitration. Also, its 3-position of the pyridine nucleus can be subjected to other electrophilic substitution reactions. Further, the halogen atom at 5-position can be changed into other functional groups. Accordingly, this material is quite useful as a raw material for synthesizing substituted pyridines. While the 2-amino-3-nitro-5-halogenopyridine (V) produced by the method of the present invention can effectively be used for making 2,3-diaminopyridines when reduced, it is also useful for making 2-substituted-3-aminopyridines when the amino group at 2-position is substituted to another substituent and then reduced.

EXAMPLES

In the following, the present invention is explained in detail by Examples.

The conditions for mechanical analyses in Examples are as follows:

Gas chromatography

Column: Silicone OV-17, 1m×3mm glass column with a carrier of Chromosorb W-AW DMCS 60–80 meshes Column temperature: 100°–260° C. with temperature raising by 10° C./min Detector and detector temperature: FID, 270° C. Carrier gas and flow rate: $N_2$, 30 ml/min $^1$H-NMR Internal standard material: Tetramethylsilane (TMS)

Solvent: Heavy DMSO ($d^6$-dimethylsulfoxide)

FT-IR

KBr pill method

EXAMPLE 1

Synthesis of 2-acetamido-4-mehtyl-5-bromopyridine (IIa) and 2-acetamido-4-methylpyridinium hydrobromide perbromide (IIIa) by bromination of 2-acetamido-4-methylpyridine (Ia)

Into a 100 ml three-neck flask, 5.0 g (0.033 mol) of Ia was introduced. Then, 15 ml of dichloromethane was added thereto so as to dissolve Ia. Thereafter, 5.34 g (0.33 mol) of bromine was added dropwise thereto. An orange-colored slurry was formed. After being stirred overnight at room temperature, the slurry was filtered under reduced pressure. When the cake obtained by the filtration was dried, 5.5 g (yield: 88%) of IIIa was obtained. After the pH of the mother liquor after the filtration under reduced temperature was adjusted to 9–10 with 5% sodium hydroxide aqueous solution, an organic layer was separated therefrom. When the solvent was evaporated away, 3.14 g (yield: 83.1%) of IIa was obtained as a slightly brown crystal. The results of analysis of obtained IIa and IIIa were as follows:

Results of analysis of IIa

1) Melting point: 146.5°–149.5° C.

2) Elemental Analysis: Calculated value as $C_8H_9N_2OBr$ . . . C:41.95% H:3.96% Analytical value . . . C:40.87% H:3.91%

3) FT-IR ($cm^{-1}$): 3190.6, 1693.7, 1664.7, 1603.0, 1562.5, 1523.9, 1271.2

4) $^1$H-NMR (ppm): 2.09 (3H,S, $COCH_3$), 2.35 (3H, S, $CH_3$), 8.08 (1H, S, aromatic), 8.34 (1H, S, aromatic), 10.55 (1H, S, NH)

5) GC: 98.2% Results of analysis of IIIa

1) Elemental Analysis: Calculated value as $C_8H_{11}N_2OB_{r3}$. . . C:24.58% H:2.84% Analytical value . . . C:24.21% H:2.76%

2) FT-IR ($cm^{-1}$): 3094.1, 2783.5, 1689.8, 1645.4, 1614.6, 1577.9, 1244.2, 1005.0, 817.9

3) $^1$H-NMR ( ppm ): 2.27 (3H, S, COCH$_3$), 2.54 (3H, S, CH$_3$), 7.38–7.46 (2H, m, aromatic), 8.24–8.35 (1H, m, aromatic), 9.85–9.90 (1H, br, HBr$_3$), 12.04 (1H, S, NH)

EXAMPLE 2

Synthesis of mixture of 2-acetamido-4-methyl-5-bromopyridine (IIa) and 2-acetamido-4-methylpyridinium hydrobromide perbromide (IIIa) by bromination of 2-acetamido- 4-methylpyridine (Ia) and underwater processing thereof Into a 300 ml three-neck flask, 51.0 g (0.34 mol) of Ia was introduced. Then, 100 ml of tetrachlorocarbon was added thereto so as to disperse Ia. The contents were heated on a hot water bath and completely dissolved at 60° C. Then, 54.4 g (0.34 mol) of bromine was added dropwise thereto for 40 minutes at that temperature. After being reacted at that temperature for an hour, the contents were cooled to 3° C. The precipitated crystal was filtered under reduced pressure. The cake obtained by the filtration was washed with 40 ml of tetrachlorocarbon. When the washed cake was dried, 97.1 g of a slightly brown crystalline mixture of IIa and IIIa was obtained. It corresponded to 92.1% of the theoretical yield.

Then, 970 ml of water was introduced into a 2-liter three-neck flask. While being stirred at room temperature, 97.1 g of the above-obtained mixture of IIa and IIIa was added thereto. After being heated on a hot water bath and reacted for two hours at 38° C., the reaction mixture was further reacted overnight at room temperature and then reacted for two hours on a hot bath at 45° C. The color of the slurry gradually changed from orange to yellow. After being cooled to room temperature, the pH of the slurry was adjusted to 4.96 with 5% NaOH aqueous solution. Then, it was filtered under reduced pressure. The cake obtained by the filtration was washed with 40 ml of water. When the washed cake was dried, 62.4 g of IIa was obtained as pale brown powder. The yield thereof was 80.1% on the basis of Ia used.

Results of analysis of finally-obtained IIa
1) Melting point: 148°–149° C.
2) GC: 99.2%.

EXAMPLE 3

According to the operations similar to those of Example 2, 47.8 g of a mixture of IIa and IIIa was obtained from 25.0 g (0.167 mol) of Ia, 100 ml of benzene, and 26.67 g (0.167 mol) of bromine. After the mixture was processed in 470 ml of water for five hours at 40° C., 26.6 g (yield: 69.7%) of IIa was obtained. The GC purity thereof was 98.5%.

EXAMPLE 4

Bromination of 2-acetamido-4-methylpyridine (Ia) in water solvent [continuous method without separation of pyridinium complex (IIIa)]

Into a one-liter three-neck flask, 25.0 g (0.167 mol) of Ia was introduced. Then, 500 ml of water was added thereto so as to dissolve Ia. Thereafter, 26.67 g (0.167 mol) of bromine was added dropwise thereto for 20 minutes at 16°–20° C. A-yellowish orange slurry was precipitated, while a crystal with a different particle form (assumed to be IIIa) partially existed in the bottom and vessel wall of the flask. The contents were stirred overnight at room temperature and then for four hours at 40° C. After being cooled to 23° C., the pH of the mixture was adjusted to 6 with 5% sodium hydroxide aqueous solution. Then, it was filtered under reduced pressure. The cake obtained by the filtration was washed with 40 ml of water. After the washed cake was dried, 30.7 g of IIa (yield: 80.4%; GC purity: 97.6%) having pale brown color was obtained.

EXAMPLE 5

Synthesis of 2-acetamido-4-methylpyridinium hydrobromide perbromide (IIia) by reaction of 2-acetamido-4-methylpyridine (Ia) with hydrobromic acid and bromine Into a 500 ml three-neck flask, 22.5 g (0.15 mol) of Ia was introduced. Then, 120 ml of tetrachlorocarbon was added thereto so as to disperse Ia. At 20°–24° C., 38.8 g (0.23 mol) of 48% hydrobromic acid was added dropwise thereto. Thus, a white crystal was precipitated and dispersed. Then, 24 g (0.15 mol) of bromine was added dropwise thereto for 10 minutes at 24° C. The contents became an orange-colored slurry. The red color of bromine was lost. After being continuously stirred for three hours at room temperature, the slurry was filtered under reduced pressure. Then, the cake obtained by the filtration was washed with 20ml of tetrachlorocarbon. When the washed cake was dried, 58.56 g of IIia (yield: 99.8%) having orange color was obtained. When 25 g of this crystal was recrystallized from acetic acid, 21 g of IIia (recrystallization yield: 84%) was obtained as yellowish orange powder.

Results of analysis of IIia (recrystallization)
1) Elemental Analysis: Calculated value as C$_8$H$_{11}$N$_2$OBr$_3$. . . C:24.58% H:2.84% Analytical value . . . C:24.39% H:2.81%.

EXAMPLE 6

Synthesis of 2-acetamido-4-methylpyridinium hydrobromide perbromide (IIIa) by reaction of 2-acetamido-4-methylpyridine (Ia) with hydrogen bromide gas and bromine Into a 500 ml three-neck flask, 22.5 g (0.15 mol) of Ia was introduced. Then, 50 ml of benzene was added thereto to disperse Ia. After the mixture was heated to 60° C. to dissolve Ia, hydrogen bromide gas was continuously supplied thereto until the weight increase of the contents ceased. A white slurry of 2-acetamido-4-methylpyridinium hydrobromide (IVa) was formed. Then, the contents were cooled. As 24 g (0.15 mol) of bromine was added dropwise thereto, the color of the slurry changed from white to orange. After being stirred at room temperature for an hour, the slurry was filtered under reduced pressure. The cake obtained by the filtration was washed with 20 ml of benzene. When the washed cake was dried, IIIa was quantitatively obtained as yellowish orange powder.

EXAMPLE 7

Synthesis of 2-acetamido-4-methyl-5-bromopyridine (IIa) by underwater processing of 2-acetamido-4-methylpyridinium hydrobromide perbromide (IIIa)

Into a 300 ml three-neck flask, 10 g (0.025 ml) of IIIa obtained by Example 6 was introduced together with ml of water. Then, the mixture was stirred for six hours at 40° C. After the pH was adjusted to 5 with 5% sodium hydroxide, the slurry was filtered under reduced pressure. Then the cake obtained by the filtration was washed with 30 ml of water. When the washed cake was dried, 4.33 g of IIa (yield: 75.6%) was obtained as a pale brown crystal. When it was recrystallized from methanol, 3.59 g of IIa was obtained as a purified product. The melting point thereof was 148.5°–149.5° C.

EXAMPLE 8

Single step synthesis of 2-acetamido-4-methyl-5-bromopyridine (IIa) by bromination of 2-acetamido-4-methylpyridine (Ia) in aqueous solution of sodium dihydrogen phosphate ($Na_2HPO_4$)

Into a 1000 ml three-neck flask, 382 ml of water was introduced. Then, a solution in which 59.3 g (0.42 mol) of $Na_2HPO_4$ had been dissolved in 119ml of water was added thereto. The pH at this moment was 9.09. To this mixture, 25 g (0.167 mol) of 2-acetamido-4-methylpyridine (Ia) was added and dispersed therein. (The saturated aqueous solution of Ia by itself had a pH of 7.59.) Then, while the mixture was stirred at 18°–19° C., 26 7 g (0.167 mol) of bromine was added dropwise thereto for 25 minutes. At this time, the formation of reddish brown IIIa, which was observed in Example 4, was not observed. After being stirred overnight at room temperature, the contents were filtered under reduced pressure. Then, the cake obtained by the filtration was washed with water. When the washed cake was dried, 33.2 g of the aimed object, IIa, (yield: 87.0%) having slightly brown color was obtained. This crystal had a melting point of 154°–156° C. with a GC purity of 95%.

The pH of the mother liquor was 7 after the filtration under reduced pressure. Then, 5% sodium hydroxide solution was added thereto to adjust the pH to 10–11. Thereafter, the mother liquor was subjected to extraction with dichloroethane. When the extracted layer was concentrated, 41 g of a crystal containing 83% of unreacted Ia (yield: 13.0%) was collected.

As can be seen from the material balance, no side reaction was generated. The aimed IIa was obtained with a good yield by a simple operation.

EXAMPLE 9

Single step synthesis of 2-acetamido-4-methyl-5-bromopyridine (IIa) by bromination of 2-acetamido-4-methylpyridine (Ia) in aqueous solution of sodium acetate ($CH_3CO_2Na$)

Into a 300 ml three-neck flask, 155 ml of water was introduced and then a solution in which 12.3 g (0.15 mol) of $CH_3CO_2Na$ had been dissolved in 25 ml of water was added thereto. The pH at this moment was 8.8. Then, 9.0 g (0.06 mol) of 2-acetamido-4-methylpyridine (Ia) was added thereto and dispersed therein. Thereafter, 9.6 g (0.06 mol) of bromine was added dropwise thereto for 12 minutes at 19°–24° C. After being stirred overnight, the mixture was filtered under reduced pressure. The cake obtained by the filtration was washed with water. When the washed cake was dried, 11.7 g of the aimed product, IIa (yield: 85.3%), was obtained as a slightly brown crystal. This crystal had a GC purity of 93% and a melting point of 155°–157° C.

EXAMPLE 10

Synthesis of 2-amino-3-nitro-4-methyl-5-bromopyridine (Va) by nitric acid processing of 2-acetamido-4-methyl-5-bromopyridine (IIa) in sulfuric acid Into a 100 ml three-neck flask, 32 ml of concentrated sulfuric acid was introduced and then cooled with iced water. At 7°–13° C., 9.16g (0.04mol) of IIa was added. Then the mixture was heated to 31° C. and 2.6 ml of concentrated nitric acid was added thereto for an hour. The mixture was further reacted at 31°–32° C. for two hours. The contents were dispersed in 100 ml of iced water. Then, the pH thereof was adjusted to 5 with concentrated aqueous ammonia. The yellow crystal formed thereby was filtered under reduced pressure and then washed with 50 ml of water. When the washed crystal was dried, 8.08 g of Va (yield: 87.1%) having a GC purity of 96.3% was obtained. When this crystal was recrystallized from water-methanol, 6.0 g of a purified product (recrystallization yield: 74%) was obtained.

Results of analysis of Va (recrystallization)

1) Melting point: 170°–172.5° C. (168°–169° C. in literature*)
2) GC: 99.3%
3) FT-IR ($cm^{-1}$): 3479.9, 3287.0, 1633.9, 1581.8, 1512.3, 1321.4, 1223.0, 870.0, 779.3

* H. Graboyes et al., J. Am. Chem. Soc., 76, 6421 (1957).

EXAMPLE 11

Synthesis of 2-amino-3-nitro-4-methyl-5-bromopyridine (Va) with 20wt % decrease of concentrated sulfuric acid Into a 500 ml of three-neck flask, 128 ml of concentrated sulfuric acid was introduced. Then, 45.8 g (0.2 mol) of 2-acetamido-4-methyl-5-bromopyridine (IIa) was added at 6°–17° C. Thereafter, 13 ml of concentrated nitric acid was added thereto at 25°–26° C. After being reacted at 27°–33° C. for four hours, the mixture was stirred overnight at room temperature. Thus obtained reaction liquid having dark brown color was poured into a beaker containing 500 ml of iced water and then the pH thereof was adjusted to 1 with 10% sodium hydroxide aqueous solution. A yellow slurry was precipitated. Then it was filtered under reduced pressure. The cake obtained by the filtration was washed with water. When the washed cake was dried, 28.8 g of Va (yield: 62.1%; GC purity: 100%) was obtained.

Further, the pH of the mother liquor obtained after the filtration was adjusted to 5. The crystal precipitated thereby was filtered under reduced pressure and then washed with water. When the washed crystal was dried, 4.4 g of Va was obtained as a crude product.

EXAMPLE 12

Synthesis of 2-amino-4-methyl-5-bromopyridine (VIa) by acidic hydrolysis of 2-acetamido-4-methyl-5-bromopyridine (IIa)

Into a 100 ml Erlenmeyer flask, 50 ml of 1N hydrochloric acid was introduced. While the mixture was stirred by a magnetic stirrer, 2.29 g (0.01 mol) of IIa was added thereto. The mixture was heated on a hot plate and reacted at 100° C. for two hours. Then, it was cooled to room temperature. Then, the pH thereof was adjusted to 10 with 25% sodium hydroxide. The crystal precipitated thereby was filtered under reduced pressure and washed with water. After the washed crystal was dried, 1.87 g of VIa (yield: 100%) was obtained as a white crystal. When it was recrystallized from methanol, 0.49 g of a purified product was obtained.

Results of analysis of VIa (recrystallization)

1) Melting point: 149.5°–151° C. (147°–147.5° C. in literature*)
2) GC: 100%

3) FT-IR (cm$^{-1}$): 3435.5, 3306.3, 3163.5, 1649.3, 1597.2, 1541.3, 1475.7, 1439.0, 1032.0, 854.5, 696.4

* H. Graboyes et al., J. Am. Chem. Soc., 76, 6421 (1957).

EXAMPLE 13

Synthesis of 2-acetamidopyridinium-HBr$_3$ complexes (III)

In a manner similar to that of Example 5, 2-acetamidopyridinium-HBr$_3$ complexes (III) were synthesized by reactions of 2-acetamidopyridines (I) with hydrobromic acid and bromine. The results are shown in Table 1.

TABLE 1

Synthesis of 2-acetamidopyridinium-HBr$_3$ complexes (III)

| Compound No. | R$_1$ | Yield (%) | FT-IR (cm$^{-1}$) | $^1$H-NMR (ppm) | Elemental analysis (%) Calculated | Analyzed |
|---|---|---|---|---|---|---|
| IIIb | 6-CH$_3$ | 83.6 | 3029, 2841, 1686, 1642, 1626, 1576, 1439, 1236, 824. | 2.23 (3H, s, COCH$_3$) 2.62 (3H, s, CH$_3$) 7.27–8.30 (3H, m, arom.) 9.29 (1H, s, HBr$_3$) 11.43 (1H, s, NH) | C: 24.5 H: 2.84 | C: 25.0 H: 2.82 |
| IIIc | 4.6–CH$_3$ | 90.3 | 3057, 2922, 1649, 1618, 1580, 1235, 1192, 856. | | Br: 59.9 | Br: 59.2 |
| IIId | H | 81.6 | 1699, 1645, 1618, 1570, 1431, 1329, 1242, 1200, 773. | 2.28 (3H, s, COCH$_3$) 7.54–7.67 (2H, m, arom.) 8.25–8.49 (2H, m, arom.) 11.16 (1H, s, HBr$_3$) 12.04 (1H, s, NH) | C: 22.3 H: 2.39 | C: 22.1 H: 2.34 |

EXAMPLE 14

Synthesis of 2-acetamido-5-bromo-6-methylpyridine (IIb) by underwater processing of 2-acetamido-6-methylpyridinium-HBr$_3$ complex(IIIb)

In a manner similar to that of Example 7, IIIb obtained by Example 13 was processed in water. The aimed product, IIb, was obtained with an yield of 74%.

Results of analysis of IIb

1) Melting point: 155.5°–157° C.

2) Elemental analysis Calculated value as C$_8$H$_9$N$_2$OBr . . . C:41.95% H:3.96% Analytical value . . . C:41.89% H:3.96%

3) FT-IR (cm$^{-1}$): 3239, 1669, 1539, 1435, 1383, 1300, 1127, 1028, 831, 802

4) $^1$H-NMR (ppm): 2.10 (3H, s, COCH$_3$) 2.50 (3H, s, CH$_3$) 7.87 (2H, s, aromatic) 10.57 (1H, s, NH)

EXAMPLE 15

Single step synthesis of 2-acetamido-5-bromopyridines (II) by bromination of 2-acetamidopyridines (I) in hydrogen disodium phosphate (Na$_2$HPO$_4$) aqueous solution In a manner similar to that of Example 8, 2-acetamidopyridines (I) was brominated and thereby 2-acetamido-5-bromopyridines (II) was synthesized. The results are shown in Table 2.

TABLE 2

Synthesis of 2-acetamido-5-bromopyridines (II)

| Compound No. | $R_1$ | Yield (%) | M.P. (°C.) | FT-IR (cm$^{-1}$) | $^1$H-NMR (ppm) |
|---|---|---|---|---|---|
| IIb | 6-CH$_3$ | 87.8 | 156–157 | Same as Example 14 | Same as Example 14 |
| IIc | 4.6-CH$_3$ | 94.8 | 218–219 (Lit. 216–217)[1] | 3239, 3052, 1671, 1562, 1447, 1397, 1275, 1181, 1028, 1001, 799. | |
| IId | H | 81.6 | 169–171 (Lit. 175)[2] | 3243, 1663, 1574, 1537, 1454, 1375, 1302, 829, 774. | 2.11 (3H, s, COCH$_3$) 7.98–8.04 (2H, m, arom.) 8.39–8.42 (1H, m, arom.) 10.64 (1H, s, NH) |

[1] R. P. Mariella, E. P. Belcher, J. Am. Chem. Soc., 74, 1916 (1952) T. Batkowski, M. Tuszynska, Rocz. Chem., 38.585 (1964)
[2] Placek, Shcharda. Chem. Ber. 61, 1815 (1928) Okamoto et al., Chem. Pharm. Bull., 14, 523 (1966)

EXAMPLE 16

Synthesis of 2-amino-5-bromopyridines (VI) by acidic hydrolysis of 2-acetamido-5-bromopyridines (II)

In a manner similar to that of Example 12, 2-acetamido-5-bromopyridines (II) obtained by Example 15 was hydrolyzed under an acidic condition and thereby 2-amino-5-bromopyridines (VI) were obtained. The results are shown in Table 3.

TABLE 3

2-amino-5-bromopyridines (VI)

| Compound No. | $R^1$ | Reaction Condition Temp. (°C.) | Time (hr) | Yield (%) | M.P. (°C.) Determined | Literature | FT-IR (cm$^{-1}$) |
|---|---|---|---|---|---|---|---|
| VIb | 6-CH$_3$ | 100 | 4 | 77.5 | 81.5–82.5 | 82.5–83.5[1] | 3362, 3196, 1640, 1582, 1456, 1404, 1331, 1032, 810, 750, 702. |
| VIc | 4.6-CH$_3$ | 100 | 4 | 85.0 | 145–146 | 145–146[2] | |
| VId | H | 100 | 4 | 75.0 | 132–134 | 132–135[3] | 3453, 3297, 3152, 1628, 1589, 1549, 1485, 1389, 1142, 1090, 1001, 826, 671, 632, 515. |

[1] A. D. Dunn. et al., J. Prakt. Chem., 331, 369 (1989)
[2] R. P. Mariella, E. P. Belcher, J. Am. Chem. Soc., 74, 1916 (1952) T. Batkowski, M. Tuszynska, Rocz. Chem. 38, 585 (1964)
[3] B. A. Fox, T. L. Threlfall, Org. Synth., Col. Vol. 5, 346

EXAMPLE 17

Synthesis of 2-amino-3-nitro-5-bromopyridines (V) by nitric-acid processing of 2-acetamido-5-bromopyridines (II) in sulfuric acid In a manner similar to that of Example 10, 2-acetamido-5-bromopyridines (II) obtained by Example 15 was processed with nitric acid in sulfuric acid and thereby 2-amino-3-nitro-5-bromopyridines (V) were synthesized. The results are shown in Table 4.

TABLE 4

2-amino-3-nitro-5-bromopyridines (V)

| Compound No. | $R_1$ | Reaction Condition Temp. (°C.) | Time (hr) | Yield (%) | M.P. (°C.) Determined | Literature | FT-IR (cm$^{-1}$) |
|---|---|---|---|---|---|---|---|
| Vb | 6-CH$_3$ | 25–30 | 5 | 80.5 | 211–213 | 210–211[1] | 3426, 3285, 3165, 1628, 1562, 1483, 1337, 1240, 847, 542. |
| Vc | 4.6-CH$_3$ | 25–30 | 5 | 86.7 | 169–170 | 168–170[2] 169–170[1] | 3447, 3299, 3173, 1634, 1574, 1545, 1498, 1325, 1242, 851, 498. |
| Vd | H | 25–30 | 7 | 75.0 | 201–203 | 204–208[3] | 3470, 3071, 1676, 1642, 1589, 1553, 1510, 1335, 1223, 910, 532. |

[1] Graboyes, Day, J. Am. Chem. Soc., 79, 6421 (1957)
[2] T. Batkowski, M. Tuszynska, Rocz. Chem. 38, 585 (1964)
[3] B. A. Fox, T. L. Threlfall, Org. Synth., Col. Vol. 5, 346

EXAMPLE 18

Synthesis of 2-acetamido-5-bromo-4,6-dimethylpyridine (IIc) by underwater processing of 2-acetamido-4,6-dimethylpyridinium-HBr$_3$ complex (IIIc)

In a manner similar to that of Example 7 or Example 14, IIIc obtained by Example 13 was processed in water and thereby the aimed product, IIc, was obtained with a yield of 75%. The physical properties thereof were the same as those of the results of IIc shown in Table 2 concerning Example 15.

EXAMPLE 19

Synthesis of 2-propionamido-5-bromopyridine (IIe)

To 47.5g of an aqueous solution containing 0.2 mol of 2-propionamido pyridine (Ie), a solution containing 71 g (0.5 ml) of disodium hydrogenphosphate dissolved in 450 g of water was added. To this mixture, a solution containing 49.2 g (0.31 mol) of bromine dissolved in 50 g of acetic acid was added with stirring at 10°–15° C. for 4 hours. After having been stirred at room temperature for one hour and then at 60° C. for one hour, the mixture was cooled. The crystal precipitated thereby was filtered. After the crystal was washed with water and dried, 38.8 g (yield: 84.7%) of 2-propionamido-5-bromopyridine (IIe) was obtained as a dark white crystal.

Results of analysis of IIe

1) Melting point: 137°–138° C.
2) FT-IR (cm$^{-1}$): 3246 (NH), 1674 (C=O)
3) $^1$H-NMR (ppm): 1.34 (3H, t, J=7.9 Hz, CH$_3$) 2.54 (2H, q, J=7.4 Hz, CH$_2$) 7.88 (1H, dd, J=8.9 Hz and 2.5 Hz, aromatic) 8.25 (1H, s, br, NH) 8.29 (1H, s, aromatic) 8.39 (1H, sd, J=2.5 Hz, aromatic)

EXAMPLE 20

Synthesis of 2-butanamido-5-bromopyridine (IIf)

To 53.6 g of an aqueous solution containing 0.2 mol of 2-butanamido pyridine (If), a solution containing 71 g (0.5 mol) of disodium hydrogenphosphate dissolved in 490 g of water was added. To this mixture, a solution containing 54.2 g (0.34 mol) of bromine dissolved in 54 g of acetic acid was added with stirring at 10°–17° C. for 5 hours. After having been stirred at room temperature for one hour and then at 60° C. for one hour, the mixture was cooled. The crystal precipitated thereby was filtered. After the crystal was washed with water and dried, 43.7 g (yield: 89.8%) of 2-butanamido-5-bromopyridine (IIf) was obtained as a pale brown crystal.

Results of analysis of IIf

1) Melting point: 111°–112° C.
2) FT-IR (cm$^{-1}$): 3279 (NH), 1699 (C=O)
3) $^1$H-NMR (ppm): 1.11 (3H, t, J=7.4 Hz, CH$_3$) 1.80–1.94 (2H, m, CH$_2$) 2.49 (2H, t, J=7.4 Hz, CH$_2$) 7.92 (1H, dd, J=8.9 Hz and 2.5 Hz, aromatic) 8.29 (1H, s, br, NH) 8.32 (1H, s, aromatic) 8.40 (1H, sd, J=2.5 Hz, aromatic)

EXAMPLE 21

Synthesis of 2-acylamino-4-methyl-5-bromopyridines (IIg–i)

In 530 g of water, 0.2 mol of a 2-acylamino-4-methylpyridine (Ig–i) was dissolved. To the resulting solution, 71 g (0.5 mol) of disodium hydrogenphosphate was added. To this mixture, a solution containing 35.2 g (0.22 mol) of bromine dissolved in 35 g of acetic acid was added with stirring at 7°–15° C. for 2 hours. After having been stirred at room temperature for one hour and then at 60° C. for one hour, the mixture was cooled. The crystal precipitated thereby (IIg–h) was filtered. After the crystal was washed with water and dried, aimed 2-acylamino-4-methyl-5-bromopyridines (IIg–h) were obtained. In the case where no crystal was precipitated (IIi), the mixture was extracted with dichloromethane, washed with 2% sodium hydroxide, and then evaporated. The results are shown in Table 5.

TABLE 5

| | Synthesis of 2-acylamino-4-methyl-5-bromopyridines (IIg–i) | | | | | | |
|---|---|---|---|---|---|---|---|
| Compound No. | R$_1$ | R$_2$ | X | Yield (%) | M.P. (°C.) | FT-IR (cm$^{-1}$) | $^1$H-NMR (ppm) |
| IIg | 4-CH$_3$ | CH$_2$CH$_3$ | Br | 94.9 | 127–129 | 3300 (NH) 1676 (C=O) | 1.18 (3H, t, J=7.4Hz, CH$_3$) 2.33 (3H, s, CH$_3$) 2.35 (2H, q, J=7.4Hz, CH$_2$) 7.84 (1H, s, br, NH) 8.11 (1H, s, aromatic) 8.20 (1H, s, aromatic) |
| IIh | 4-CH$_3$ | (CH$_2$)$_2$CH$_3$ | Br | 98.0 | 75–77 | 3275 (NH) 1698 (C=O) | 1.11 (3H, t, J=7.4Hz, CH$_3$) 1.79–1.93 (2H, m, CH$_2$) 2.49 (2H, t, J=7.4Hz, CH$_2$) 2.51 (3H, s, CH$_3$) 8.18 (1H, s, br, NH) 8.30 (1H, s, aromatic) 8.37 (1H, s, aromatic) |
| IIi | 4-CH$_3$ | (CH$_2$)$_3$CH$_3$ | Br | 92.6 | 73–74 | 3272 (NH) 1698 (C=O) | 1.05 (3H, t, J=7.4Hz, CH$_3$) 1.44–1.58 (2H, m, CH$_2$) 1.73–1.87 (2H, m, CH$_2$) 2.48 (2H, t, J=7.4Hz, CH$_2$) 8.00 (1H, s, br, NH) 8.28 (1H, s, aromatic) 8.37 (1H, s, aromatic) |

EXAMPLE 22

Synthesis of 2-acetamido-5-chloropyridine (IIj)

In 300 ml of water, 13.6 g (0.1 mol) of 2-acetamidopyridine (Id) was dissolved. To this solution, 35.5 g (0.25 mol) of disodium hydrogenphosphate and 100 ml of dichloromethane were added in this order. While this mixture was stirred, 8.0 g (0.11 mol) of chlorine was introduced thereto at 0° C. for 30 minutes. Then the mixture was further stirred at the same temperature for 2 hours. After the mixture was brought back to room temperature, it was separated into a water layer and an extract layer. Thereafter, the water layer was further extracted with 100 ml of dichloromethane and then washed with saturated brine. The resulting extract layer was dehydrated by sodium sulfate anhydride. When dichloromethane was evaporated off, 16.0 g (yield: 94.0%) of 2-acetamido-5-chloropyridine (IIj) was obtained as a pale brown crystal.

Results of analysis of IIj

1) Melting point: 171°–172° C.

2) FT-IR (cm$^{-1}$): 3239 (NH), 1665 (C=O)

3) $^1$H-NMR (ppm): 2.31 (3H, S, COCH$_3$) 7.76 (1H, dd, J=8.9 Hz and 2.5 Hz, aromatic) 8.18 (1H, s, br, NH) 8.29 (1H, d, J=8.4 Hz, aromatic) 8.31 (1H, sd, J=2.5 Hz, aromatic)

stirred at the same temperature for 2 hours, the mixture was separated into a water layer and an extract layer. After the water layer was further extracted with 100 ml of dichloromethane, the newly-separated extract layer was combined with the previously-separated extract layer and washed with saturated brine. Then the washed mixture was desiccated with sodium sulfate anhydride. When the solvent was evaporated off, 18.0 g (yield: 97.3%) of 2-acetamido-4-methyl-5-chloropyridine (IIk) was obtained as a pale yellow crystal.

Results of analysis of IIk

1) Melting point: 152°–153° C.

2) FT-IR (cm$^{-1}$): 3260 (NH), 1669 (C=O)

3) $^1$H-NMR (ppm): 2.27 (3H, s, COCH$_3$) 2.50 (3H, s, CH$_3$) 8.20 (1H, s, br, NH) 8.23 (1H, s, aromatic) 8.25 (1H, s, aromatic)

EXAMPLE 24

Synthesis of 2-amino-5-halogenopyridines (VI) by acidic hydrolysis of 2-acylamino-5-halogenopyridines (IIe–k)

In a manner similar to that of Example 12, the 2-acylamino-5-halogenopyridines (IIe–k) obtained by Examples 19–23 were hydrolyzed under an acidic condition and thereby 2-amino-5-halogenopyridines (VI) were obtained. The results are shown in Table 6.

TABLE 6

| | | | | | | | | |
|---|---|---|---|---|---|---|---|---|
| | | | | | Synthesis of 2-amino-5-halogenopyridines (VI) | | | |
| Material No. | $R_1$ | $R_2$ | X | Product No. | $R_1$ | X | Yield (%) | M.P. (°C.) |
| IIe | H | CH$_2$CH$_3$ | Br | VId | H | Br | 83.6 | 131–133 |
| IIf | H | (CH$_2$)$_2$CH$_3$ | Br | VId | H | Br | 79.4 | 132–134 |
| IIg | 4-CH$_3$ | CH$_2$CH$_3$ | Br | VIa | 4-CH$_3$ | Br | 94.8 | 148–149 |
| IIh | 4-CH$_3$ | (CH$_2$)$_2$CH$_3$ | Br | VIa | 4-CH$_3$ | Br | 90.5 | 147–149 |
| IIi | 4-CH$_3$ | (CH$_2$)$_3$CH$_3$ | Br | VIa | 4-CH$_3$ | Br | 82.7 | 147–149 |
| IIj | H | CH$_3$ | Cl | VIe | H | Cl | 89.2 | 136–137 (136–137[1]) |
| IIk | 4-CH$_3$ | CH$_3$ | Cl | VIf | 4-CH$_3$ | Cl | 95.8 | 150–152 (149–151[1]) |

[1] T. J. Kress, L. L. Moore, S. M. Costantio, J. Org. Chem., 41, 93 (1976)

EXAMPLE 23

Synthesis of 2-acetamido-4-methyl-5-chloropyridine (IIk)

In 300 ml of water, 15.0 g (0.1 mol) of 2-acetamido-4-methylpyridine (Ia) was dissolved. To this solution, 35.5 g (0.25 mol) of disodium hydrogenphosphate and 100 ml of dichloromethane were added in this order. While this mixture was stirred, 8.0 g (0.11 mol) of chlorine was introduced thereto at 0° C. for one hour. After having further been

EXAMPLE 25

Synthesis of 2-amino-3-nitro-5-halogenopyridines (V) by nitric acid processing of 2-acylamino-5-halogenopyridines (IIe–k) in sulfuric acid In a manner similar to that of Example 10, the 2-acylamino-5-halogenopyridines (IIe–k) obtained by Examples 19–23 were processed with nitric acid in sulfuric acid and thereby 2-amino-3-nitro-5-halogenopyridines (V) were obtained. The results are shown in Table 7.

TABLE 7

| | | | | | | | | |
|---|---|---|---|---|---|---|---|---|
| | | | | | Synthesis of 2-amino-3-nitro-5-halogenopyridines (V) | | | |
| Material No. | $R_1$ | $R_2$ | X | Product No. | $R_1$ | X | Yield (%) | M.P. (°C.) |
| IIe | H | CH$_2$CH$_3$ | Br | Vd | H | Br | 79.6 | 202–203 |
| IIf | H | (CH$_2$)$_2$CH$_3$ | Br | Vd | H | Br | 75.6 | 201–203 |
| IIg | 4-CH$_3$ | CH$_2$CH$_3$ | Br | Va | 4-CH$_3$ | Br | 84.3 | 169–171 |
| IIh | 4-CH$_3$ | (CH$_2$)$_2$CH$_3$ | Br | Va | 4-CH$_3$ | Br | 82.2 | 170–172 |
| IIi | 4-CH$_3$ | (CH$_2$)$_3$CH$_3$ | Br | Va | 4-CH$_3$ | Br | 78.5 | 169–171 |
| IIj | H | CH$_3$ | Cl | Ve | H | Cl | 73.4 | 199–200 |

TABLE 7-continued

| | Synthesis of 2-amino-3-nitro-5-halogenopyridines (V) | | | | | | | |
|---|---|---|---|---|---|---|---|---|
| Material No. | $R_1$ | $R_2$ | X | Product No. | $R_1$ | X | Yield (%) | M.P. (°C.) |
| IIk | 4-$CH_3$ | $CH_3$ | Cl | Vf | 4-$CH_3$ | Cl | 75.7 | (198[1])[2] |

[1] T. Batkowski, Rocz. Chem., 42, 2079 (1968)
[2] Melting Point: 146–147° C.
IR ($cm^{-1}$): 3490 (NH), 3287 (NH), 1645 (C=O), 1522 ($NO_2$), 1323 ($NO_2$)
$^1$H-NMR (ppm, DMSO): 2.38 (3H, s, $CH_3$)
7.09 (2H, s, br, $NH_2$)
8.23 (1H, s, aromatic)

As evidenced by the foregoing Examples, 2-amino-3-nitro-5-halogenopyridines can be produced quite efficiently in accordance with the present invention in which a 2-acylaminopyridine is used as a starting material and a 2-acylamino-5-halogenopyridine is formed as an intermediate.

What is claimed is:

1. A method of producing a 2-acylamino-5-bromopyridine expressed by formula (II)

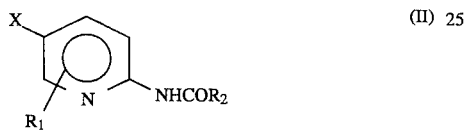
(II)

wherein $R_1$ is hydrogen or at least one lower alkyl group connected to the 4-position and/or the 6-position, $R_2$ is an alkyl group or an unsubstituted or substituted phenyl group, and X is bromine, said method comprising the steps of processing a 2-acylaminopyridinium-$HBr_3$ salt expressed by formula (III)

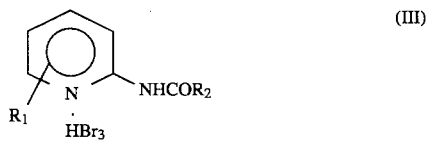
(III)

wherein $R_1$, $R_2$, and X are defined in the same manner as in the formula (II), by gradually decomposing said 2-acylamino-pyridinium-$HBr_3$ salt in a protic polar solvent selected from the group consisting of water and alcohol at a temperature between room temperature and 60° C. to form a slurry of said 2-acylamino-5-bromopyridine of formula (II); subjecting said slurry to solid-liquid separation to separate the 2-acylamino-5-bromopyridine solid; and purifying said solid to obtain the 2-acylamino-5-bromopyridine of formula (II).

2. The method of claim 1 wherein said 2-acylaminopyridinium-$HBr_3$ salt of formula (III) is formed by the steps of reacting a 2-acylaminopyridine expressed by formula (I)

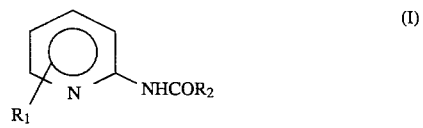
(I)

wherein $R_1$ and $R_2$ are defined in the same manner as in formula (II) with gaseous hydrogen bromide or concentrated hydrobromic acid in the presence of an organic solvent to form a 2-acylaminopyridinium-HBr salt expressed by formula (IV)

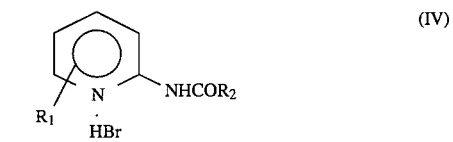
(IV)

wherein $R_1$ and $R_2$ are defined in the same manner as in formula (I); and continuously adding bromine to said salt of formula (IV) to form said 2-acylaminopyridinium-$HBr_3$ salt of formula (III).

3. The method described in claim 2, wherein the organic solvent is selected from the group consisting of chain hydrocarbons, hydrocarbon halides and aromatic organic compounds.

4. The method described in claim 3, wherein said organic solvent is selected from the group consisting of n-hexane, n-octane, n-heptane, dichloromethane, dichloroethane, trichloroethane, chloroform, carbon tetrachloride, benzene, chlorobenzene, o-dichlorobenzene and nitrobenzene.

* * * * *